United States Patent [19]

Ruger et al.

[11] Patent Number: 5,834,224
[45] Date of Patent: Nov. 10, 1998

[54] ELECTROCHEMICAL SENSOR CONTAINING AN ENZYME LINKED TO BINDING MOLECULES BOUND TO A NOBLE METAL SURFACE

[75] Inventors: Petra Ruger, Penzberg; Dorothee Ambrosius; Bernd Schmidt, both of Munich; Peter Sluka, Weilheim; Hans-Joachim Guder, Grunstadt; Erhard Kopetzki, Penzberg, all of Germany

[73] Assignee: Boehringer Mannhein GmbH, Mannhein, Germany

[21] Appl. No.: 519,300

[22] Filed: Aug. 23, 1995

[30] Foreign Application Priority Data

Aug. 24, 1994 [DE] Germany ............... 44 30 023.9

[51] Int. Cl.⁶ .............. C12Q 1/54; C12N 11/14; G01N 27/327; C12M 1/34
[52] U.S. Cl. .............. 435/14; 204/403; 435/18; 435/25; 435/172.3; 435/176; 435/177; 435/181; 435/190; 435/287.1; 435/817
[58] Field of Search ................. 435/14, 18, 25, 435/174, 176, 177, 180, 181, 285.2, 287.1, 817, 172.3, 190; 204/403

[56] References Cited

U.S. PATENT DOCUMENTS 5,601,694  2/1997  Maley et al. ............ 204/415

FOREIGN PATENT DOCUMENTS

| 0524722 | 1/1993 | European Pat. Off. . |
| 0583894 | 2/1994 | European Pat. Off. . |
| 0584794 | 3/1994 | European Pat. Off. . |
| 8912624 | 12/1989 | WIPO . |
| 9208788 | 5/1992 | WIPO . |
| 9210757 | 6/1992 | WIPO . |

OTHER PUBLICATIONS

O. Okumura, et al., "Cleaning composition," *Chemical Abstracts*, vol. 84, No. 20 (May 17, 1976).

A. Mederos, et al., "El acido dicarboximetil–N, N–Metionina," *Anales De Quimica*, Bd. 75, Nr. 6 (1979).

Primary Examiner—David M. Naff
Attorney, Agent, or Firm—Fulbright & Jaworski

[57] ABSTRACT

An electrochemical sensor is provided containing a supporting material having a surface of noble metal such as gold or palladium to which is bound an enzyme such as glucose oxidase via binding molecules. The binding molecules are in the form of a homogenous monolayer and are bound to the metal surface by anchor groups such as thiol, disulphide or phosphine groups. The enzyme is linked to the binding molecules by an ionic bond, a covalent bond or a metal-chelate bond. The binding molecules may contain a spacer such as an alkylene chain. Coverage of the binding molecules on the metal surface is less than the maximum coverage to optimize enzyme coverage, decrease response time of the sensor and increase signal yield per surface area. The monolayer may contain diluent molecules which are not linked to an enzyme and which are bound to the metal surface via anchor groups. The diluent molecules lower the concentration of binding molecules in the monolayer, increase conductivity of the monolayer and lower unspecific binding of components from a sample solution in contact with the sensor. The binding molecules can be linked by an ionic bond or a metal-chelate bond, respectively, to a charged amino acid residue or a chelate-forming amino acid residue of the N-terminus, C-terminus, or N- and C-terminus of recombinant enzyme protein.

25 Claims, 9 Drawing Sheets compound A compound B compound C compound D

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: oligonucleotide ( v i ) ORIGINAL SOURCE:
        ( A ) ORGANISM: Aspergillus niger ( v i i ) IMMEDIATE SOURCE:
        ( B ) CLONE: YEpL/AD-GOD ( x i ) SEQUENCE DESCRIPTION: SEQ ID NO: 1:

C G C G T C G G C C     G G T C G A C G                                                         1 8

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: other nucleic acid
(A) DESCRIPTION: oligonucleotide (xi) SEQUENCE DESCRIPTION: SEQ ID NO: 2:

GATCCGTCGA CCGGCCGA  18

(2) INFORMATION FOR SEQ ID NO: 3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: oligonucleotide (vi) ORIGINAL SOURCE:
(A) ORGANISM: Aspergillus niger (vii) IMMEDIATE SOURCE:
(B) CLONE: YEpL/GOD-(His)4Cys (xi) SEQUENCE DESCRIPTION: SEQ ID NO: 3:

CAGCACCACC ACCACTGTTG AATTCAG  27

(2) INFORMATION FOR SEQ ID NO: 4:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: oligonucleotide (xi) SEQUENCE DESCRIPTION: SEQ ID NO: 4:

CTGAATTCAA CAGTGGTGGT GGTGCTGCAT G  31

(2) INFORMATION FOR SEQ ID NO: 5:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: other nucleic acid
(A) DESCRIPTION: oligonucleotide (vi) ORIGINAL SOURCE:
(A) ORGANISM: Aspergillus niger (vii) IMMEDIATE SOURCE:
(B) CLONE: YEpL/GOD-Cys (xi) SEQUENCE DESCRIPTION: SEQ ID NO: 5:

CAGTGTTAAT GAATTCAG  18

(2) INFORMATION FOR SEQ ID NO: 6:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: oligonucleotide -continued ( x i ) SEQUENCE DESCRIPTION: SEQ ID NO: 6:

CTGAATTCAT TAACACTGCA TG                      22

ELECTROCHEMICAL SENSOR CONTAINING AN ENZYME LINKED TO BINDING MOLECULES BOUND TO A NOBLE METAL SURFACE

FIELD OF THE INVENTION

The invention concerns an electrochemical sensor containing a supporting material which has a noble metal surface and an enzymatically active protein which is adsorptively bound to the noble metal surface.

BACKGROUND OF THE INVENTION

The application of enzyme sensors for the determination of an analyte by electrochemical measurement is known (see for example Turner et al., Biosensors, Fundamentals and Application (1987), Oxford University Press).

DESCRIPTION OF THE INVENTION

The immobilization of enzymes on the sensor surface has previously usually been accomplished by enclosure behind and in membranes, binding to polymers and cross-linking with bifunctional reagents. These methods have the disadvantage that the enzyme molecules are statistically distributed in a thick layer on the solid phase. As a result diffusion of the analyte to the reactive centre of the enzyme and diffusion of the product to the electrode is inhibited, the reaction time of the sensor is long and the sensitivity is low. A further disadvantage of this type of immobilization is that, when the enzyme is covalently bound to the sensor surface, loss of activity often occurs due to changes in the active centre. The above-mentioned methods for binding the enzyme to the solid phase are described for example in A. Wiseman (Handbook of Enzyme Biotechnology, Alice Horwood, Chichester (1985), 2nd Edition. 166 ff) or in O. Zaborsky (Immobilised Enzymes, CRC Press, Cleveland Ohio (1974), 2nd Edition.

The production of defined thin monolayers on solid phases and the use of these monolayers for immobilizing biological components has been known for some time. Thus for example Lee et al., (Sens. Act. B, 12 (1993), 153–158) describe Langmuir-Blodgett membranes for adsorbing avidin to which a glucose oxidase labelled with biotin can subsequently be bound. FR-A-2682765 discloses the combined application of glucose oxidase and amphiphilic molecules in the Langmuir-Blodgett method. The use of lipid bilayers in sensors is also described by Tien et al. (Crit. Rev. Biomed. Eng., 18 (1991) 323–340). A disadvantage of the Langmuir-Blodgett is their low stability.

A further possibility of producing molecular thin layers is the so-called SAM (self-assembling monolayer) technique which was described by Bain and Whitesides (Ang. Chem. 101 (1988), 522–528). Such self-assembling monolayers are formed for example by adsorption of long-chained thiols onto gold surfaces. Sawaguchi et al. (Bioelectrochemistry and Bioenergetics 29 (1992), 127–133) and Willner et al. (J. Am. Chem. Soc. 114 (1992),10965–10966) have described the immobilization of diaphorase and glutathione reductase on a metal surface by means of thiols. Collinson and Bowden (Langmuir 8 (1992), 1247–1250) disclose the immobilization of cytochrome C on a metal surface using 16-mercaptohexadecanoic acid and 11-mercaptoundecanoic acid. It was found that only a third of the surface is occupied by cytochrome C. Kinnear and Monbouquette (Langmuir 9 (1993), 2255–2257) describe the incorporation of an enzyme that absorbs directly onto the metal surface in a self-assembling monolayer.

The previously described methods for immobilizing enzymes in self-assembling monolayers have the disadvantage of a low covering density of the enzyme and a low conductivity which is associated with a low sensitivity of the resulting monolayer. In particular the problems are caused by the distance of the enzyme from the metal surface being too great when long-chained thiols are used and a substantial decrease in the homogeneity of the surface when using shorter-chained thiols. Direct adsorption of the enzyme onto the metal surface also does not lead to an adequately homogeneous layer and in addition a partial denaturation of the proteins can occur when they are directly adsorbed onto the metal.

A binding matrix is known from WO 92/10757 containing a supporting material and a solid phase reactant which is adsorbed thereto via anchor groups which is capable of binding to at least one free reaction partner characterized in that the solid phase reactant forms a diluted and essentially laterally homogeneous binding layer on the surface of the supporting material. The solid phase reactants described in WO 92/10757 are for example biotin or haptens. No examples are described in which enzymes are used as solid phase reactants.

The problem which forms the basis of the present invention was to provide an electrochemical sensor in which the disadvantages of the state of the art are at least substantially eliminated. In particular the sensor should provide a high covering density of the enzyme coupled with a high conductivity and sensitivity.

SUMMARY OF THE INVENTION

The solution for this inventive problem is achieved by an electrochemical sensor containing a supporting material which has a noble metal surface, an essentially laterally homogeneous monolayer on the surface of the supporting material which is adsorptively bound to the supporting material, wherein the monolayer comprises binding molecules which are bound to the supporting material via anchor groups, wherein the binding molecules are linked to an enzymatically active protein by means of an ionic bond, a covalent bond or a metal chelate bond and wherein the degree of coverage of the binding molecules on the supporting material is less than the maximum degree of coverage.

The degree of coverage of the binding molecules is less than the maximum degree of coverage i.e. a diluted monolayer is present with respect to the binding molecules. Coverage of the solid phase with the enzymatically active protein can be optimized by means of the degree of coverage of the binding molecules. In the optimum a densely packed enzyme layer is achieved. The degree of coverage of the monolayers with binding molecules is less than 100 % and advantageously 1–99 %, preferably 2–98 % and especially preferably 5–95 %.

As a result of the diluted layer of binding molecules adsorbed onto the supporting material, the electrochemical sensor according to the invention contains a monomolecular layer of preferably uniformly oriented enzymatically active proteins or enzymes with a maximum degree of coverage on the solid phase which leads to a decrease in the response time of the sensor and an increase in the signal yield per surface area. A further advantage of the sensor is that the monolayer can be applied by a simple immersion process. In addition the sensor according to the invention is also very suitable for multiple and continuous measurements due to the covalent binding of the enzymes.

The supporting material of the sensor according to the invention has a noble metal surface and basically all noble metals or noble metal mixtures or noble metal alloys with a standard electrode potential (i.e. a potential versus a normal hydrogen electrode $Pt/H_2$ (1 atm)/$H^+$ (a=1) as reference electrode) which is more positive than the potential of a silver electrode are suitable. Examples of suitable noble metals are Au, Pt, Pd etc.. The supporting material particularly preferably has a gold or palladium surface.

A supporting material with a noble metal surface is produced for example by vapourizing glass with chromium as an adhesive agent during which a layer of ca. 0.1–10 nm thickness is formed. This chromium layer is subsequently vapourized with the noble metal, e.g. gold, which forms a layer which represents the surface of the supporting material. This noble metal layer preferably has a thickness between 10 and 200 nm. In the case of a supporting material made of plastic (e.g. polycarbonate) it is also possible to vapourize the noble metal directly onto the support.

Adsorption of molecules onto the surface of the supporting material is mediated by anchor groups. The type of anchor group depends on the respective surface of the supporting material. Thiol, disulphide or/and phosphine groups are especially suitable as anchor groups. Thiol or/and disulphide groups are for example particularly suitable as anchor groups for a gold surface and phosphine groups are particularly suitable for a palladium surface.

Reference is made to WO 92/10757 for different methods of producing diluted binding layers. In a first embodiment the monolayer consists of a single type of molecule and the surface is not completely occupied by anchor groups. Such a layer can for example be manufactured by immersing the surface in a solution which contains a very low concentration (e.g. $<1\times10^{-5}$ mol/l) of binding molecules. In this manner a diluted film of binding molecules is obtained on the surface, on which the enzyme can be subsequently immobilized.

In a preferred embodiment of the invention the monolayer additionally contains diluent molecules, apart from the binding molecules, which are adsorptively bound to the supporting material via anchor groups and are not linked to an enzymatically active protein. The production of a monomolecular layer of binding and diluent molecules is achieved by immersing the surface in a solution which contains the binding and diluent molecules in their desired molar ratios. The enzyme can be subsequently immobilized on this coated surface.

When manufacturing the sensor, the molar ratio of binding molecules to diluent molecules is preferably in the range of 1:100 to 100:1, particularly preferably of 1:50 to 50:1 and most preferably of 1:20 to 20:1. In particular applications of the sensor according to the invention it may be preferable to have a molar ratio of binding molecules to diluent molecules which is larger than 1:1 and in particular 5:1 to 20:1.

The use of diluent molecules not only optimizes the enzyme coverage but it surprisingly also considerably increases the conductivity of the layer which is an important criterium for electrical applications. In addition the diluent molecules lower the unspecific binding of components from a sample solution which is in contact with the sensor.

The enzymatically active protein which is linked to the binding molecule by means of an ionic bond, a covalent bond or a metal-chelate bond is preferably selected from the group of enzymes that catalyse a reaction in which compounds are formed or/and consumed that can be detected electrochemically. Such a reaction can be monitored electrochemically e.g. potentiometrically or amperometrically. Preferably these are enzymes which catalyse reactions in which ions are formed or/and consumed, in which $H_2O_2$ is formed or/and in which electrochemical mediators are converted. Examples of such enzymes are oxidoreductases i.e. enzymes which can oxidize or/and reduce a substrate molecule. However, hydrolases and enzymes in which a pH change occurs during their reaction are also suitable.

A preferred example of a suitable enzyme is a glucose oxidase (EC 1.1.3.4). Glucose oxidase from the microorganism *Aspergillus niger* is for example commercially available from the Boehringer Mannheim GmbH Company, GFR.

The enzymatically active protein can, however, also be a recombinant enzyme i.e. an enzyme which is obtained from a heterologous host cell. An advantage of such recombinant enzymes is that they can be used in a modified form by genetic manipulation which enables improved immobilization on the sensor surface. Examples of suitable modifications are the N- or/and C-terminal attachment of one or several amino acid residues selected from basic amino acids such as for example arginine or lysine, acidic amino acids such as for example aspartate or glutamate, chelate-forming amino acids such as for example histidine or cysteine.

The enzyme can be covalently or ionically linked to the binding molecule or by means of a metal-chelate bond. An ionic binding of the enzyme can be based on the chemistry of ion or cation exchangers. In this embodiment of the invention the binding molecules are linked to the enzymatically active protein by means of an ionic bond, the binding occurring between a charged end group of the binding molecule and an oppositely charged region of the enzymatically active protein. Thus the charged end group of the binding molecule can for example comprise at least one amino function and the oppositely charged region of the enzymatically active protein can comprise at least one acidic amino acid residue, preferably a series of e.g. 2 to 8 aspartate or glutamate residues. On the other hand the charged end group of the binding molecule can comprise at least one carboxylate or/and preferably sulfonate function and the oppositely charged region of the enzyme can comprise at least one basic amino acid residue, preferably a series of e.g. 2 to 8 arginine or/and lysine residues. An advantage of immobilizing enzymes in this manner is that it enables an oriented binding of the enzyme to the solid phase. A further advantage is that the active centre of the enzyme is not impeded when the region reacting with the binding molecule is a section attached to the N- or/and C-terminus of the enzyme.

In a further embodiment of the invention the enzyme can be covalently linked to the binding molecule, the binding occurring between a reactive end group of the binding molecule and a reactive group of the enzymatically active protein. A preferred example of a reactive end group of the binding molecule is a maleimide group which can react with a cysteine residue of the enzyme. A further example of a covalent binding is the binding of phenol residues of the enzyme to a diazonium group in the binding molecule. It is also possible to couple oxidized sugar residues of the enzyme to amino end groups of the binding molecule. A comprehensive review of possible covalent immobilization agents which could be used in the sensors according to the invention is given in the afore-mentioned references of Wiseman and Zaborsky. Reference is hereby made to this disclosure.

Enzymes can also be immobilized by binding via metal chelates in which binding occurs between a chelate-forming end group of the binding molecule, a metal ion and a chelate-forming region of the enzymatically active protein.

The chelate-forming end group of the binding molecule can for example comprise a dicarboxylate or tricarboxylate group and the chelate-forming region of the enzymatically active protein can comprise a series of adjacent histidine residues. Examples of suitable chelate-forming metal ions are e.g. nickel, iron, cobalt, copper and zinc ions. An oriented binding of enzymes to the solid phase is also possible when the binding is by means of metal chelates.

It is also preferred for a sensor according to the invention that the binding molecule contains a spacer between the anchor group and the end group capable of binding to the enzymatically active protein. The length of the spacer between the anchor group and the binding site for the enzyme can exert a considerable influence on the function of the sensor. Variations in the length can influence the conductivity as well as the accessibility of the binding sites to the enzyme. The spacer is preferably an alkylene chain with a length of 4–30 atoms which may contain heteroatoms e.g. S, N or/and O atoms. The spacer particularly preferably contains 1–4 $C_2$–$C_4$ alkylene oxide units, preferably 1–4 ethylene oxide units.

Like the binding molecules, the diluent molecules contain an anchor group suitable for adsorption to the solid phase i.e. a thiol, disulphide or/and phosphine group. The other end group of the diluent molecules is preferably a hydrophilic function e.g. a hydroxyl, $C_1$–$C_4$ alkoxy, an amino, a carboxyl, a carboxylic acid ester or a carboxylic acid amide function. A spacer as defined above is preferably located between the end group and the anchor group of the diluent molecule. The spacer for the diluent molecules preferably contains up to 15 atoms and at least one ethylene oxide unit.

The production of genetically modified proteins which, as a result of a modification especially at the C-or/and N-terminus, can be bound to a solid phase in a uniform orientation and a solid phase with the oriented immobilized protein is disclosed in WO 92/08788. Metal-chelate binding or ionic binding as a possible immobilization method for enzymes is not disclosed. Stayton et al. (J. Am. Chem. Soc. 114 (1992), 9298–9299) describe the oriented binding of cytochrome C by genetic modification and direct binding of the cysteine residue introduced on the surface of the enzyme to a gold surface. A disadvantage of this method is that no other group that adsorbs to the metal surface may be present on the surface of the enzyme. Since, however, hydrophobic surfaces such as metals often have a high unspecific adsorption of proteins, the use of the aforementioned enzyme sensors would be expected to have major disadvantages.

A subject matter of the invention is therefore also an electrochemical sensor containing a supporting material which has a noble metal surface, an essentially laterally homogeneous monolayer on the surface of the supporting material that is bound adsorptively to the supporting material, wherein the monolayer comprises binding molecules that are bound to the supporting material by means of anchor groups wherein the binding molecules are linked by means of an ionic bond to at least one and preferably a series of charged amino acid residues at the N- or/and C-terminus of an enzymatically active protein.

The present invention in addition concerns an electrochemical sensor containing a supporting material which has a noble metal surface, an essentially laterally homogeneous monolayer on the surface of the supporting material that is bound adsorptively to the supporting material, wherein the monolayer comprises binding molecules that are bound to the supporting material by means of anchor groups wherein the binding molecules are linked by means of a metal-chelate bond to at least one and preferably a series of adjacent chelate-forming amino acid residues at the N- or/and C-terminus of an enzymatically active protein.

The present invention additionally concerns methods for the determination of an analyte in a sample solution wherein the sample solution is incubated with a sensor according to the invention under conditions which lead to an electrochemically detectable reaction of the analyte and the reaction of the analyte is determined by an electrochemical measurement e.g. by a potentionmetric or amperometric measurement.

A preferred example of an analyte is glucose in which case a sensor with an immobilized glucose oxidase is used for the determination. A glucose oxidase modified by recombinant DNA technology with a N- or/and C-terminal attachment of acidic, basic, chelate-forming amino acids or/and cysteine residues is particularly preferably used.

Yet a further subject matter of the present invention is a compound of the general formula

in which A denotes a HS or $H_2P$ group and n denotes 1 or A denotes a -SS group and n is 2, Sp denotes a spacer with a chain length of 4–30 atoms and X is a maleimide group or a group with at least two positive or negative charges e.g. a guanidinium group or a group of formula (II)

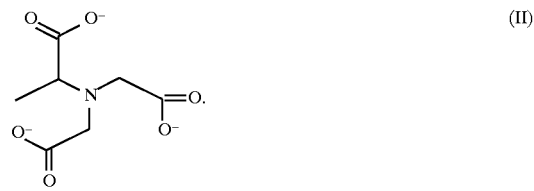

Such compounds are preferably used to manufacture electrochemical sensors.

In addition the present invention is elucidated further by the following examples in conjunction with FIGS. 1–7 and the sequence protocols.

Figure 1A:
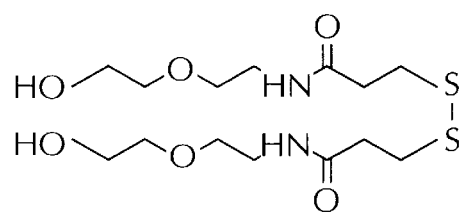
FIG. 1: shows
a) a diluent molecule (compound A)
b) a binding molecule with a biotin group (compound B)
c) a binding molecule with a chelate-forming end group (compound C)
d) a binding molecule with a reactive maleimide end group (compound D)
Figure 1B:
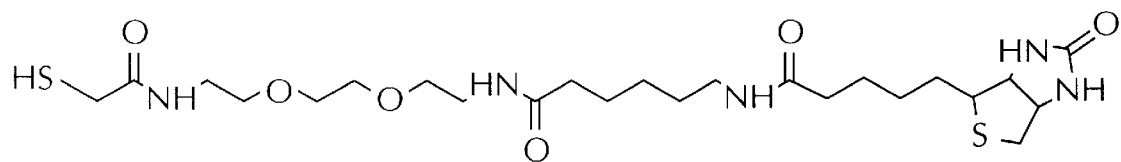
Figure 1C:
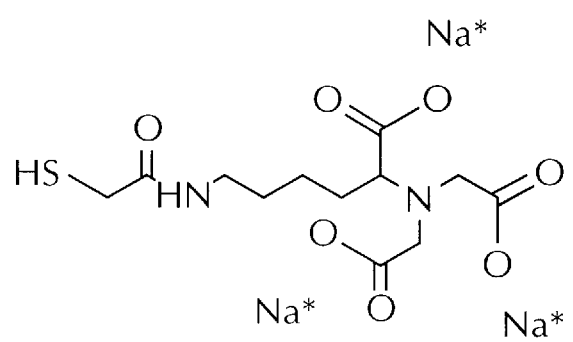
Figure 1D:
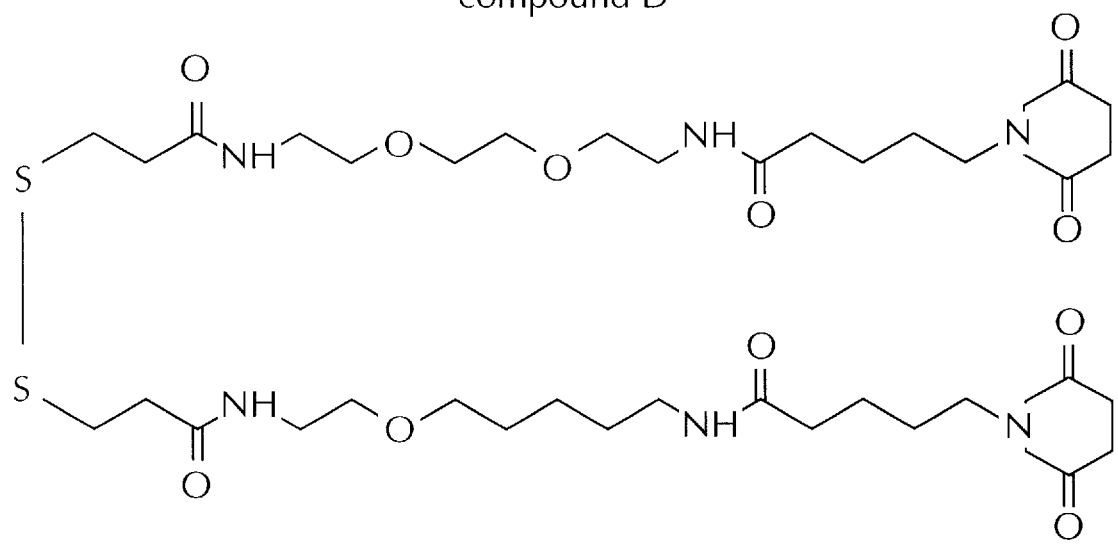

SEQ ID NO: 1: shows primer (1) used for the construction of plasmid the YEpl/AD-GOD (example 1.1)

SEQ ID NO: 2: shows primer (2) used for the construction of the plasmid YEpl/AD-GOD (example 1.1)

SEQ ID NO: 3: shows primer (3) used for the construction of the plasmid YEpl/GOD-(His)$_4$Cys (example 1.3)

SEQ ID NO: 4: shows primer (4) used for the construction of the plasmid YEpl/GOD-(His)$_4$Cys (example 1.3)

SEQ ID NO: 5: shows primer (5) used for the construction of the plasmid YEpl/GOD-Cys (example 1.4)

SEQ ID NO: 6: shows primer (6) used for the construction of the plasmid YEpl/GOD-Cys (example 1.4)

The expression plasmid YEpL/GOD-(His)$_4$ contains a GOD gene with 4 additional C-terminal His residues. The isolation and enzymatic characterization of GOD-(His)$_4$ are described in DE-A-43 01 904 (examples 4, 7 and 8.

1.3 Production of GOD-(His)$_4$ Cys 1.3.1 Construction of the plasmid YEpL/GOD-(His)$_4$Cys The plasmid contains a modified GOD gene which codes for a GOD enzyme variant that has 4 additional histidine residues and one cysteine residue at the C-terminus.

The plasmid YEpL/GOD-(His)$_4$Cys was constructed from the plasmid YEpL/AD-GOD using 2 complementary oligonucleotides in a similar manner to plasmid GOD-(His)$_4$.

For this plasmid YEpL/AD-GOD was cleaved with SphI and PvuII, the ca. 10.2 kBp long SphI/PvuII-YEpL/GOD vector fragment was isolated and ligated with the following DNA linkers which were constructed from 2 oligonucleotides by hybridization.

Primer (3): 5'-CAGCACCACCACCACTGTTGAATTCAG-3'   (SEQ ID NO. 3)
Primer (4): 5'-CTGAATTCAACAGTGGTGGTGGTGCTGCATG-3' (SEQ ID NO. 4)

```
    SphI                              EcoRI
5'-      CAGCACCACCACCACTGTTGAATTCAG-3'
3'-GTACGTCGTGGTGGTGGTGACAACTTAAGTC-5'
    ----Gln His His His His Cys Stop
```

DESCRIPTION OF THE PREFERRED EMBODIMENTS

EXAMPLE 1

Production of modified glucose oxidase (GOD) molecules 1.1 Construction of the plasmid YEpL/AD-GOD The expression plasmid YEpL/AD-GOD is derived from the plasmid YEpL/GOD (production and description see DE-A-43 01 904, example 1.1–1.5). Plasmid YEpL/GOD contains the GOD gene from Aspergillus niger and is suitable for recombinant expression and secretion of GOD in *Saccharomyces cerivisiae*.

The non-essential positive regulator gene MAL2-8cp in YEpL/GOD (stimulates the α-glucosidase promoter used for GOD expression) was replaced by a polylinker for construction-related technical reasons. This enables the construction of C-terminal GOD fusion proteins by means of a SphI restriction cleavage site that is now present singularly.

For this plasmid YEpL/GOD was digested with the restriction endonucleases BamHl and Mlul, the ca. 10.2 kBp long BamHl/Mlul-YEpL/GOD vector fragment was isolated and ligated with the following DNA linkers which were constructed from 2 oligonucleotides by hybridization.

Primer (1): 5'-CGCGTCGGCCGGTCGACG-3'   (SEQ ID NO. 1)
Primer (2): 5'-GATCCGTCGACCGGCCGA-3'   (SEQ ID NO. 2)

```
Mlul    Ec1XI    SalI   BamHI
5'-CGCGTCGGCCGGTCGACG-3'
3'-    AGCCGGCCAGCTGCCTAG-5'
```

The desired plasmid YEpL/AD-GOD was identified by restriction mapping and analyzed further.

1.2 Production of GOD-(His)$_4$

The desired plasmid YEpL/GOD-(His)$_4$Cys was identified by restriction mapping (new EcoRI cleavage site) and analysed further by partial sequencing (C-terminal region of GOD structural gene).

1.3.2. Expression, purification and enzymatic characterization of GOD-(His)$_4$Cys The expression, purification and enzymatic characterization was carried out as described for GOD-(His)$_4$ described in DE-A-43 01 904 (examples 4, 7 and 8).

1.4. Production of GOD-Cys 1.4.1 Construction of the plasmid YEpL/GOD-Cys

The plasmid contains a modified GOD gene which codes for a GOD enzyme variant that has an additional cysteine residue at the C-terminus.

The plasmid YEpL/GOD-Cys was constructed from the plasmid YEpL/AD-GOD using 2 complementary oligonucleotides in a similar manner to plasmid GOD-(His)$_4$Cys.

For this the plasmid YEpL/AD-GOD was cleaved with SphI and PvuII, the ca. 10.2 kBp long SphI/PvuII fragment was isolated and ligated with the following DNA linkers which were constructed from 2 oligonucleotides by hybridization.

Primer (5): 5'-CAGTGTTAATGAATTCAG-3'   (SEQ ID NO. 5)
Primer (6): 5'-CTGAATTCATTAACACTGCATG-3' (SEQ ID NO. 6)

```
    SphI            EcoRI
5'-      CAGTGTTAATGAATTCAG-3'
3'-GTACGTCACAATTACTTAAGTC-5'
    ----Gly Cys Stop
```

The desired plasmid YEpL/GOD-Cys was identified by restriction mapping (new EcoRI cleavage site) and analysed further by partial sequencing (C-terminal region of GOD structural gene).

1.4.2. Expression. purification and enzymatic characterization of GOD-(His)$_4$CyS The expression, purification and enzymatic characterization was carried out as described for GOD-(His)$_4$ in DE-A-43 01 904 (examples 4, 7 and 8).

The C-terminal GOD fusion proteins GOD-(His)$_4$, GOD-(His)$_4$-Cys and GOD-Cys behave like the unmodified GOD enzyme in yeast (in wild-type and glycosylation-defective yeast strains) with regard to secretion, glycosylation, amount of carbohydrate, specific activity, thermostability and pH stability.

EXAMPLE 2

Synthesis of a diluent molecule

A. 2(S-Acetyl)mercaptopropionic acid-2-(2-hydroxyethoxy) ethylamide.

A solution of 5 g (20 mmol) N-succinimidyl-S-acetylthiopropionate (synthesized according to example 28 of WO-A-92/10757) in 50 ml THF was added dropwise to a solution of 2.14 g (20 mmol) 2-(2-aminoethoxy)ethanol in 25 ml THF within a time period of 15 minutes and stirred for 2 hours at 20° C. After completion of the reaction (monitored by TLC), the reaction mixture was concentrated by evaporation in a vacuum and purified by chromatography on silica gel.

Yield 2.7 g
TLC: silica gel 60
Eluent: ethyl acetate/methanol=7:3+1% acetic acid
RF=0.67
MS (pos FAB): MH$^+$–236

B. 2-Mercaptopropionic acid-[2-(2-hydroxyethoxy)] ethylamide 600 ml of a 1 mol/l solution of hydroxylamine in methanol was added to 2.7 g (8.7 mmol) of the compound synthesized in "A" and stirred for one hour at 20° C. Then the solvent was evaporated in a vacuum and the residue was extracted three times with dichloromethane. 1.5 g of an oily crude product was obtained and purified by flash chromatography on silica gel. This compound can be used as a diluent molecule.

Yield: 0.86 g (colourless oil)
TLD: silica gel 60,
eluant: dichloromethane/methanol=9/1
RF=0.45
MS (pos. FAB): MH$^+$=194

C. The disulphide compound (compound A) was synthesized by oxidation from the thiol compound synthesized in

EXAMPLE 3

Synthesis of a chelate-forming binding molecule (compound C)

28 g bromoacetic acid was dissolved in 75 ml 2N NaOH and cooled to 0° C. N-Boc-L lysine was dissolved in 75 ml 2N NaOH and slowly added dropwise to the bromoacetic acid. After the dropwise addition, the ice-bath was removed, it was heated to 70° C. and stirred for a further 2 hours. The solution was concentrated to half the volume and subsequently admixed with 300 ml 1N HCl. In this process a white precipitate forms. The preparation was allowed to stand for 3–4 hours at 4° C., suction filtered and the residue was washed once with ice water and dried. The substance (15.3 g) was subsequently suspended in 100 ml chloroform. 20 ml trifluoroacetic acid was added and stirred for 2 hours at room temperature. Chloroform and trifluoroacetic acid were removed in a high vacuum and the viscous residue was admixed with 100 ml ether and stirred until a white solid precipitated. The substance was suction filtered, washed and dried (yield 15.3 g). 1.5 g of this substance was dissolved in 30 ml methanol and 1.62 g triethylamine. 0.92 g N-succinimidyl-S-acetylthioacetate was added while stirring. It was stirred for 3 hours at room temperature and subsequently the solvent was removed. The product was purified on a silica gel column (yield 2 g). This product was afterwards dissolved under nitrogen in 40 ml 12.5% ammonia solution and stirred for 1 hour at room temperature. The solution was concentrated in a high vacuum and the product was subsequently isolated by means of column chromatography (yield 500 mg).

EXAMPLE 4

Synthesis of a binding molecule with a reactive maleimide group (compound D)

10.9 g dithiodipropionic acid, 12.7 g N-hydroxysuccinimide and 22.7 g dicyclohexylcarbodiimide were dissolved in 100 ml DMF and 100 ml dioxane and stirred for 12 hours at room temperature. Subsequently the precipitate was suction filtered and the solvent was removed. 18.5 g of an oily residue was obtained. 2.06 g of the product was dissolved in 100 ml dioxane. 2.78 g mono-N-Boc-1,8-diamino-3,6-dioxaoctane was added to this solution and stirred for 12 hours at room temperature. Afterwards the preparation was admixed with 2.2 ml trifluoroacetic acid, concentrated to ca. 20 ml on a rotary evaporator and purified by column chromatography. Ca. 4 g of an oily product was obtained after removing the solvent. This product was dissolved in 50 ml dioxane and 3.1 g maleimidohexanoyl-N-hydroxysuccinimide ester in 10 ml dioxane was added to this solution. The mixture was stirred for 12 hours at room temperature, subsequently the solvent was removed and it was purified by column chromatography. 190 mg of product was obtained as a white powder.

EXAMPLE 5 (COMPARISON)

2×40 nm gold were evaporated in succession onto polycarbonate supports. The supports were subsequently incubated for one hour in 5×10$^{-4}$ mol/l of a mixture of the biotin-compound B (synthesis: see example 29 of WO-A-92/10757) and compound A (synthesis: see example 2) in a molar ratio of 1:10 in water. After thorough washing in water, they were dried in a stream of argon.

Figure 2:
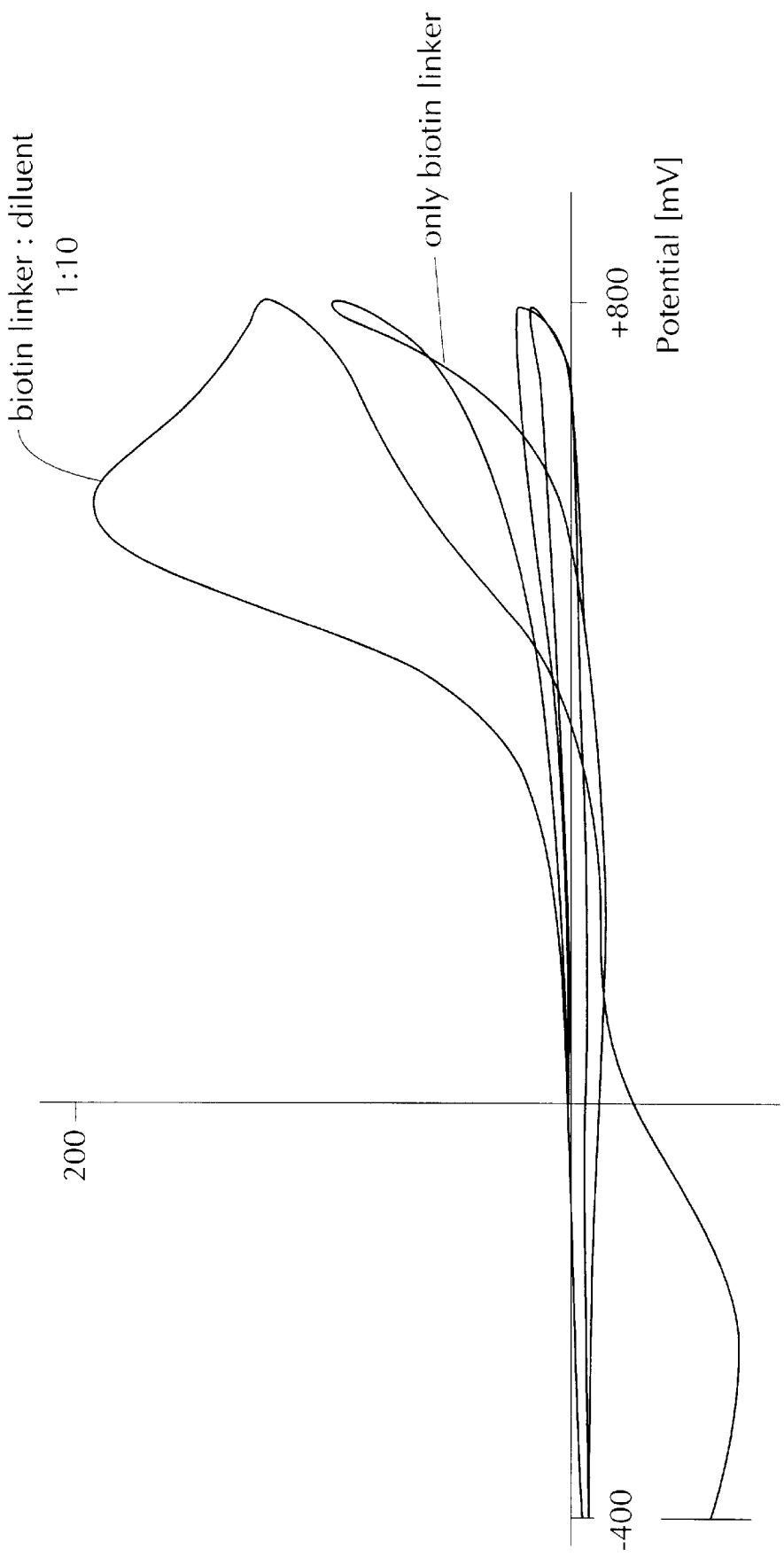
FIG. 2: shows
a cyclovoltammogram of the sensors
a) coated with pure compound B
b) coated with a mixture of compounds A and B (10:1)

The electrochemical conversion of 1 mmol/l K$_4$[Fe(CN)$_6$] and N,N-dimethylnitrosoaniline was characterized with the aid of cyclovoltammetry. Whereas an undiluted SAM of the pure compound B almost completely prevented the conversion of hexacyanoferrate, a good conductivity of the surface was produced by applying a mixed layer (FIG. 2). Surface plasmon resonance and contact angle measurements indicated a dense coverage of the surface.

The electrode coated with binding molecule (compound B) and diluent (compound A) was subsequently immersed for one hour in a solution of streptavidin (1 mg/ml) in 0.1 mol/l potassium phosphate buffer pH 7.0, rinsed with buffer and incubated for 1 hour in a solution of biotinylated glucose oxidase in the above-mentioned buffer (1 mg/ml). After again thoroughly rinsing with buffer and water, the sensor was ready to use.

The determination of the analyte, in this case glucose (10 mmol/l), was carried out amperometrically. The mediator, e.g. N-nitrosoaniline at a concentration of 1×10$^{-3}$ mol/l, was added to the sample solution and, after an incubation period of 2 min., the current was measured at an applied potential appropriate for the mediator, in this case 240 mV.

Only very small currents were obtained with this sensor when glucose was added although the GOD activity was photometrically detectable. The universal binding phase described in WO-A-92/10757 is thus not optimal for electrochemical enzyme sensors. The next examples describe the modification of the binding molecule needed to arrive at a suitable structure for electrochemical applications.

EXAMPLE 6

The gold supports corresponded to those of example 5. The supports were incubated for 1 hour in $2 \times 10^{-3}$ mol/l of a mixture of compound C (mercaptonitrilotriacetic acid) and compound A in methanol. After thorough successive washing in pure methanol and water, they were incubated for 10 minutes in a 0.2% solution of $NiCl_2$ in water, again washed several times in water and dried in a stream of argon.

Figure 3A:
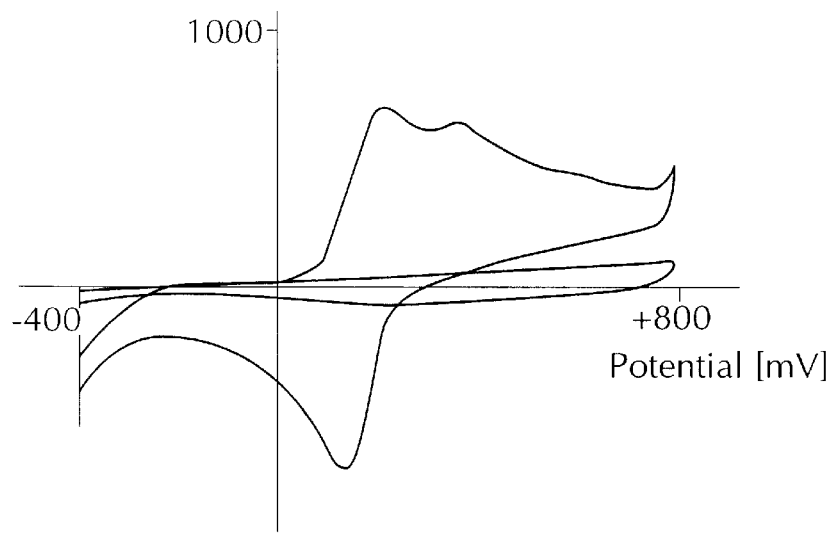
FIG. 3: shows
a cyclovoltammogram of the sensors
a) coated with pure compound C
b) coated with a mixture of compounds A and C (1:10)
Figure 3B:
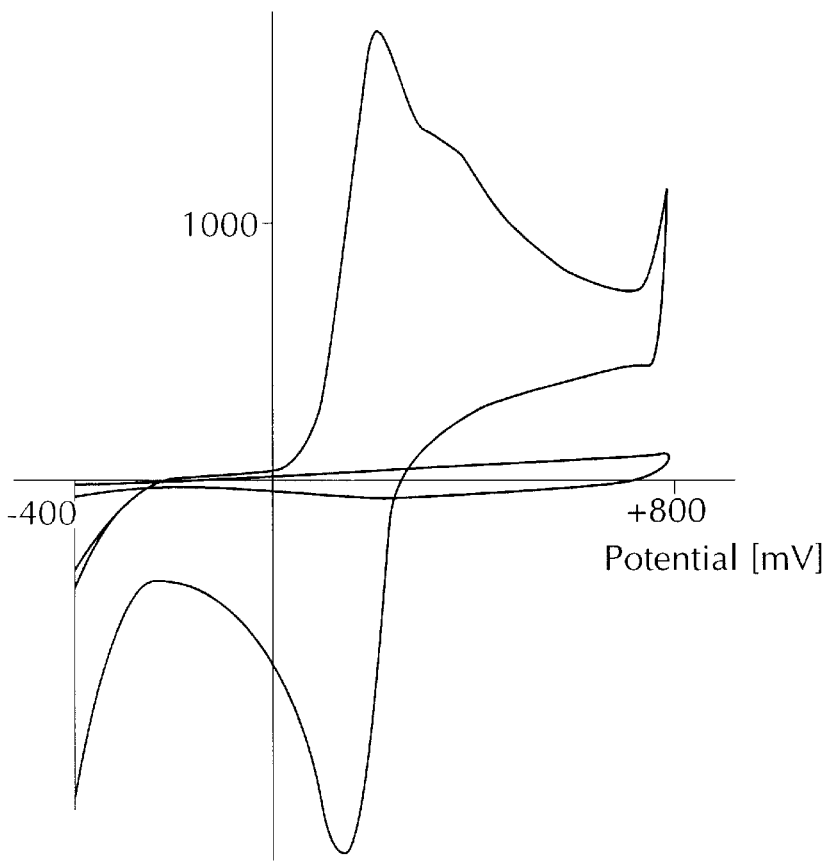

The layer was characterized with the aid of cyclovoltammetry (cf. example 5). Whereas application of the pure compound C considerably impeded the conversion of redox active substances such as $K_4[Fe(CN)_6]$, the additional binding of compound A to the gold surface resulted in a good reaction of the mediator on the electrode (FIG. 3).

Glucose oxidase modified at a genetic level that was C-terminally extended by histidine residues (cf. example 1), was bound to the solid phase via a metal-chelate bond by immersing the modified support for 1 hour in a solution of the enzyme in 0.1 mol/l potassium phosphate buffer pH 7.0.

Figure 4:
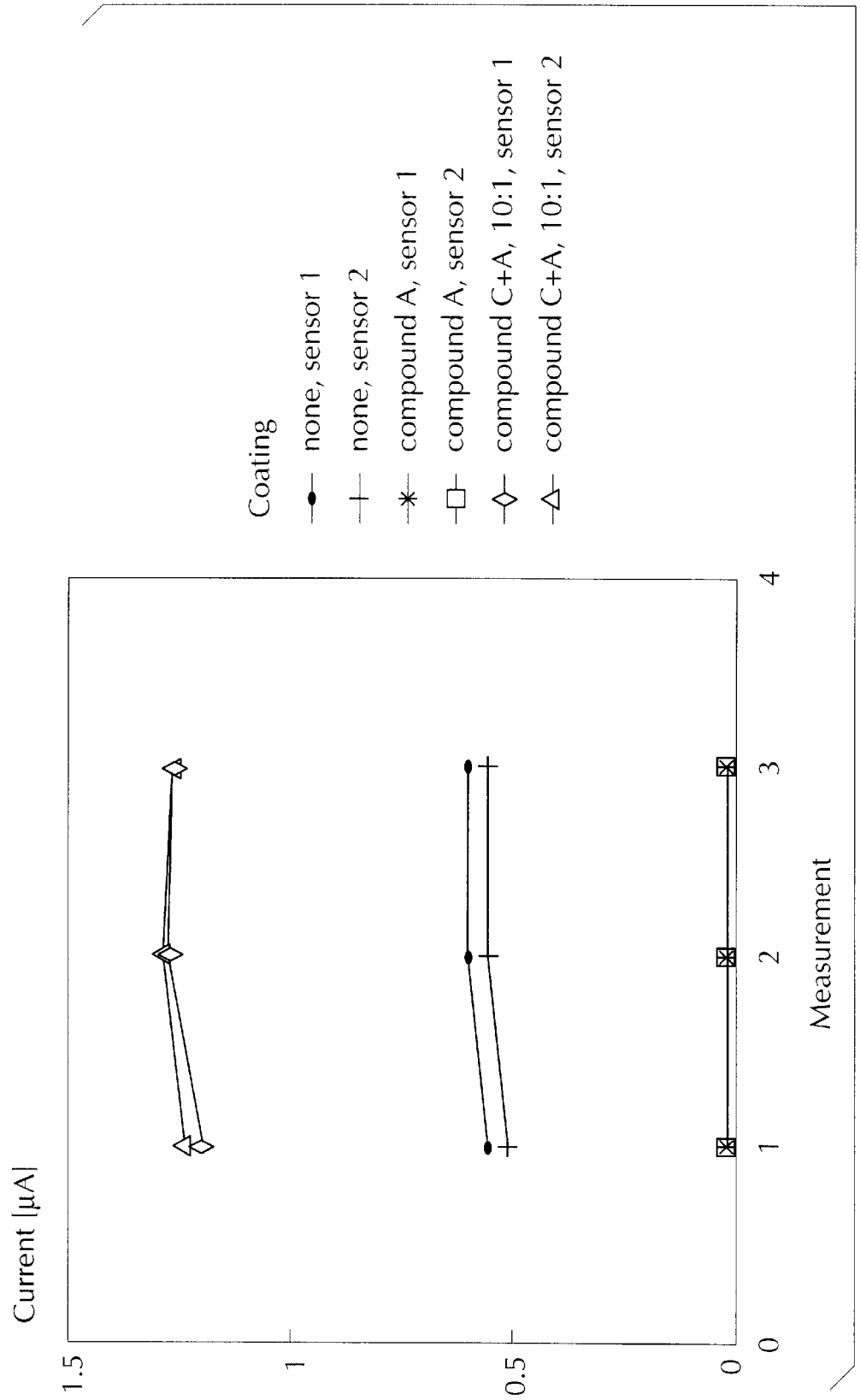
FIG. 4: shows the results of an amperometric determination of the binding of glucose oxidase-$His_4$ to uncoated gold surfaces, to gold coated with diluent molecules (compound A) and to gold coated with a chelate-forming binding molecule (compound C)
Figure 5:
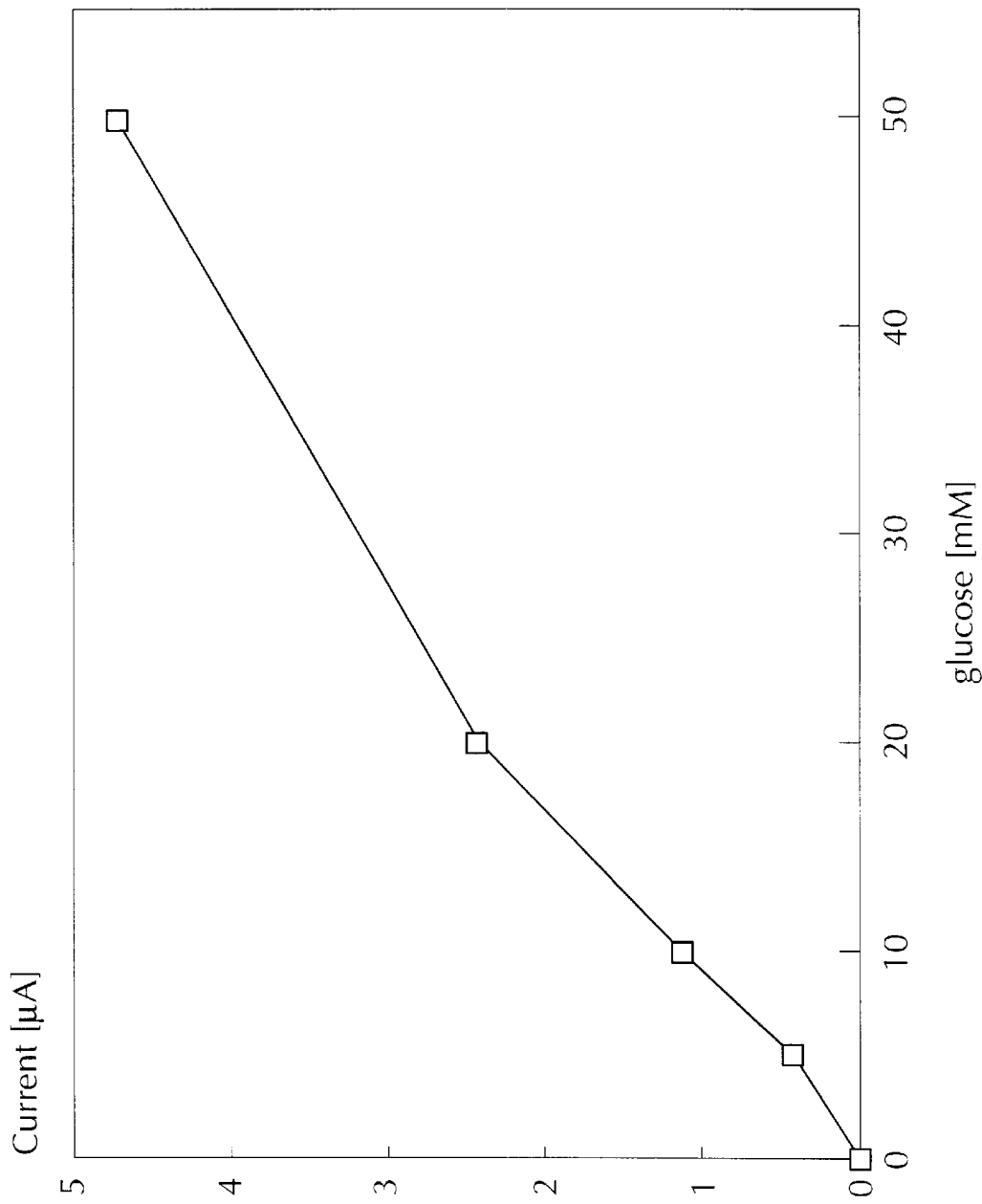
FIG. 5: shows the dependency of the current signal on the glucose concentration for a sensor according to example 6.
Figure 6:
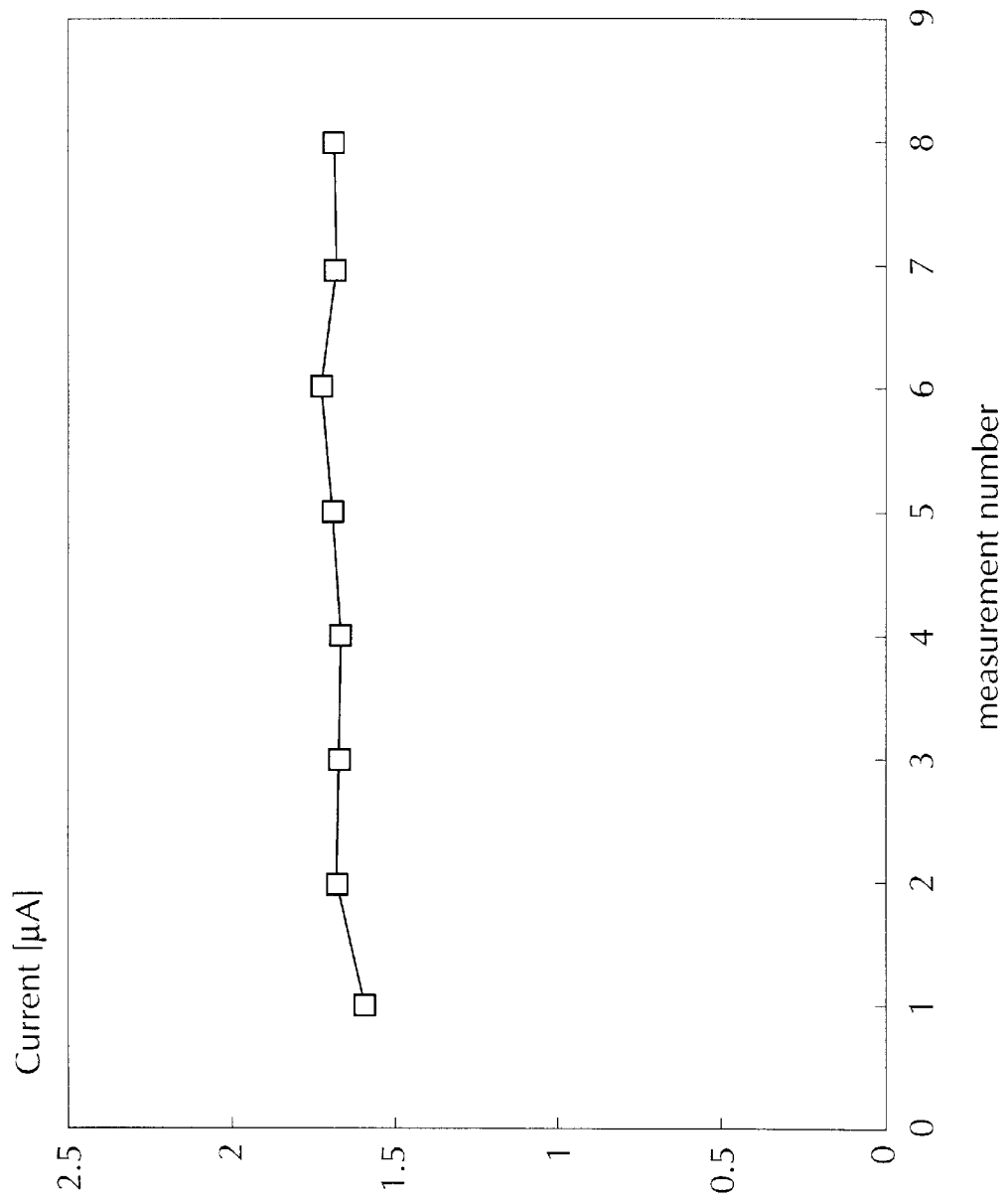
FIG. 6: shows the reproducibility of successive measurements on a sensor according to example 6.

The function-dependent evaluation was carried out as described in example 5 using a 10 mmol/l glucose solution, N,N-dimethyl-4-nitrosoaniline as a mediator and at a potential of 240 mV. FIG. 4 and Tab. 1 show that the selected sensor structure resulted in a considerably higher sensitivity than the direct immobilization of the enzyme on the gold surface and the immobilization of the pure compound C. A molar ratio of compounds C and A of 10:1 proved to be most favourable. In contrast the enzyme was not bound to surfaces of the pure compound A. The signal of a sensor which was coated with a mixture of compounds A and C was proportional to the content of glucose in the sample solution (FIG. 5). In addition the signal was stable in several consecutive measurements (FIG. 6).

EXAMPLE 7

The gold support corresponded to those of example 5. They were incubated for 1 hour in a solution of compound D ("maleimide linker") and compound A in a molar ratio of 10:1 (best results) and at a total concentration of $1 \times 10^{-3}$ mol/l in methanol. After thorough washing in methanol and water, they were dried in a stream of argon.

Figure 7:
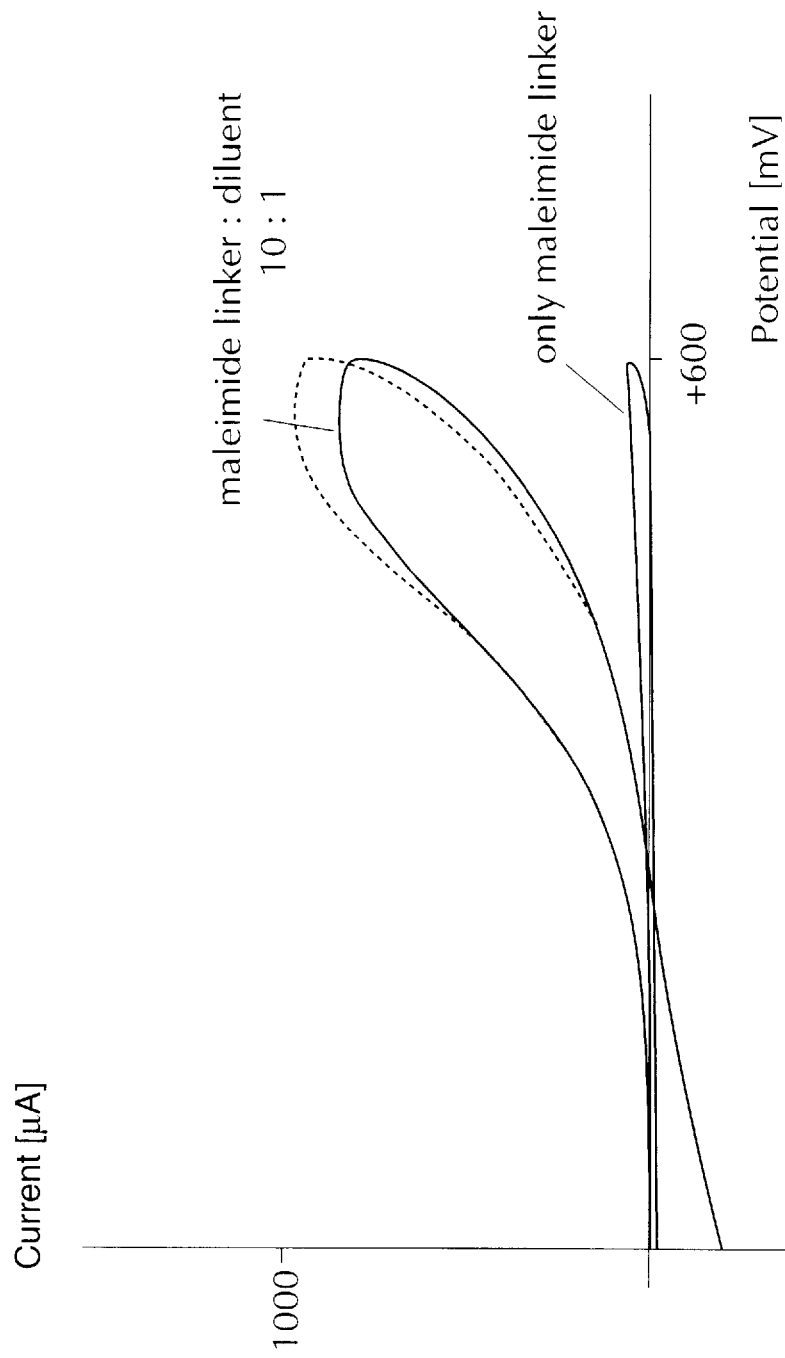
FIG. 7: shows a cyclovoltammogram of the sensors
 a) coated with pure compound D
 b) coated with a mixture of compounds A and D (1:10)

The cyclovoltammogram with 1 mmol/l $K_4[Fe(CN)_6]$ shows that the densely packed layer of the pure compound D substantially reduces the conversion of N,N-dimethylnitrosoaniline. This barrier was removed by addition of compound A and the surface had a similar activity to pure gold with regard to the redox reaction (FIG. 7).

Figure 8:
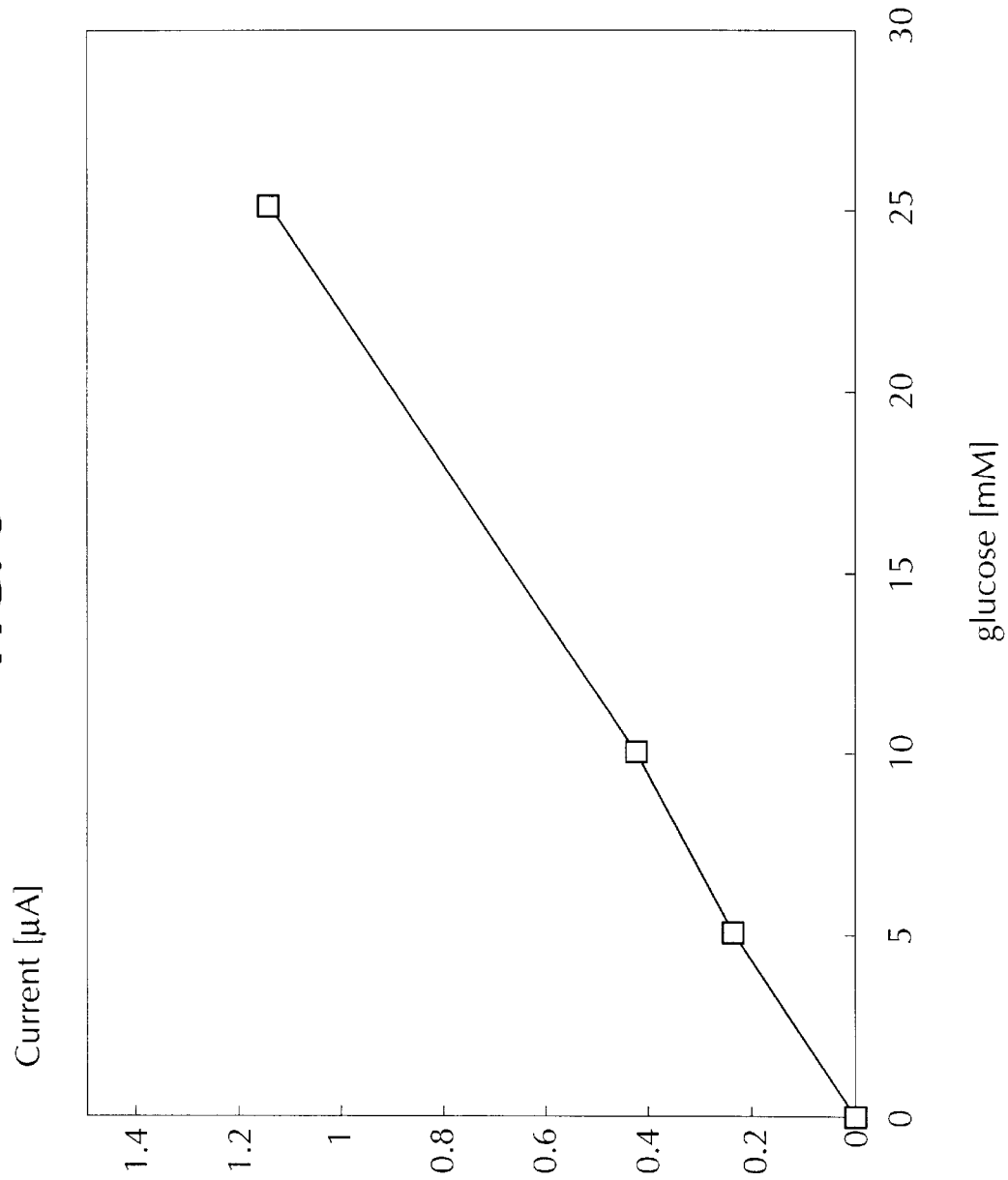
FIG. 8: shows the dependency of the current signal on the glucose concentration for a sensor according to example 7.

Subsequently the support was incubated for 1 hour in a solution of SH-modified glucose oxidase GOD-Cys (1 mg/ml) in 0.1 mol/l potassium phosphate buffer pH 7.0. In this process the enzyme was covalently bound via thiol groups to the maleimide end group of the linker. The determination of the analyte was carried out as described in example 5. FIG. 8 shows the increase in the current with the analyte concentration.

We claim:
1. An electrochemical sensor comprising a supporting material, the supporting material having a noble metal and a homogenous monolayer on the noble metal surface, the monolayer comprising binding molecule and another type of molecule which functions to lower concentration of the binding mol in the monolayer, to increase conductivity of the monolayer and to lower unspecific binding of components from a sample solution, the binding molecule and the other type of molecule being in a ratio in the monolayer of 1:100 to 100:1 and being bound to the noble metal surface via anchor groups, wherein the binding molecule is linked to an enzymatically active protein by an ionic bond a covalent bond or a metal-chelate bond and wherein the degree of coverage of the binding molecules on the metal surface is less than the maximum degree of coverage and wherein the other type of molecule is not bound to an enzymatically active protein.

2. The sensor as claimed in claim 1, wherein the noble metal surface is gold or palladium.

3. The sensor as claimed in claim 1, wherein the anchor groups are selected from the group consisting of thiol, disulphide and phosphine groups.

4. The sensor as claimed in claim 1, wherein the molar ratio of the binding molecule to the other type of molecule is in the range of 1:50 to 50:1.

5. The sensor as claimed in claim 1, wherein the molar ratio of the binding molecule to the other type of molecules is in the range of 1:20 to 20:1.

6. The sensor as claimed in claim 1, wherein the enzymatically active protein is selected from the group of enzymes which catalyse a reaction in which compounds are formed and consumed and which can be detected electrochemically.

7. The sensor as claimed in claim 6, wherein the enzymatically active protein is an oxidoreductase or hydrolase.

8. The sensor as claimed in claim 7, wherein the enzymatically active protein is a glucose oxidase (E.C.1.1.3.4).

9. The sensor as claimed in claim 1, wherein the enzymatically active protein is a recombinant enzyme.

10. The sensor as claimed in claim 9, wherein the enzymatically active protein is modified by attaching at the N- terminus, or N- and C-terminus, one or several amino acid residues selected from the group consisting of basic amino acids, acidic amino acids, chelate-forming amino acids and cysteine residues.

11. The sensor as claimed in claim 1, wherein the binding molecule is linked to the enzymatically active protein by an ionic bond in which the bond is formed between a charged end group of the binding molecule-and an oppositely charged region of the enzymatically active protein.

12. The sensor as claimed in claim 11, wherein the charged end group of the binding molecule comprises at least one amino function and the oppositely charged region of the enzymatically active protein comprises at least one aspartate residue, glutamate or aspartate and glutamate residues.

13. The sensor as claimed in claim 11, wherein the charged end group of the binding molecule comprises at least one carboxylate, sulfonate, or carboxylate and sulfonate function and the oppositely charged region of the enzymatically active protein comprises at least one arginine residue lysine residue or arginine and lysine residues.

14. The sensor as claimed in claim 1, wherein the binding molecule is linked to the enzymatically active protein by a covalent bond in which the bond is formed between a reactive end group of the binding molecule and a reactive group of the enzymatically active protein.

15. The sensor as claimed in claim 14, wherein the reactive end group of the binding molecule comprises a maleimide group and the reactive group of the enzymatically active protein comprises a cysteine residue.

16. The sensor as claimed in claim 1, wherein the binding molecule is linked to the enzymatically active protein by a metal chelate bond in which the bond is formed between a chelate-forming end group of the binding molecule, a chelate-forming metal ion-and a chelate-forming region of the enzymatically active protein.

17. The sensor as claimed in claim 16, wherein the chelate-forming end group of the binding molecule comprises a dicarboxylate or tricarboxylate group and the chelate-forming region of the enzymatically active protein comprise at least one histidine residue.

18. The sensor as claimed in claim 16, wherein the metal ion is selected from the group consisting of a nickel, iron, cobalt, copper and zinc ion.

19. The sensor as claimed in claim 1, wherein the binding molecule contains a spacer between the anchor group and an end group capable of forming a bond with the enzymatically active protein.

20. The sensor as claimed in claim 19, wherein the spacer is an alkylene chain having a length of 4–30 atoms which may contain heteroatoms.

21. The sensor as claimed in claim 1, where n said noble layer has a thickness of from about 10 to about 200 nm.

22. A method for the determination of an analyte in a sample solution, wherein the sample solution is contacted with a sensor as claimed in claim 1 under conditions which lead to an electrochemically detectable reaction of the analyte and the reaction of the analyte is determined by an electrochemical measurement.

23. The method as claimed in claim 22, wherein the analyte is glucose.

24. An electrochemical sensor comprising a supporting material, the supporting material having a noble metal surface, and a homogenous monolayer on the noble metal surface, wherein the monolayer comprises binding molecules which are bound to the noble metal surface via anchor groups, wherein the binding molecules are linked by an ionic bond to at least one charged amino acid residue at the N-terminus, C-terminus, or N- and C- terminus of an enzymatically active protein, and wherein the degree of coverage of the binding molecules on the metal surface is less than the maximum degree of coverage.

25. An electrochemical sensor containing a supporting material the supporting material having a noble metal surface, and a homogenous monolayer on the noble metal surface, wherein the monolayer comprises binding molecules which are bound to the noble metal surface via anchor groups, wherein the binding molecules are linked by a metal-chelate bond to at least one chelate-forming amino acid residue at the N-terminus, C terminus, or N- and C-terminus of an enzymatically active protein.

* * * * *

UNITED STATES PATENT AND TRADEMARK OFFICE
CERTIFICATE OF CORRECTION

PATENT NO. : 5,834,224
DATED : November 10, 1998
INVENTOR(S) : Petra Ruger, et al.

It is certified that error appears in the above-identified patent and that said Letters Patent is hereby corrected as shown below:

In column 6, line 12, change "potentionmetric" to -- potentiometric --.

In column 6, line 23, in the general formula (I), change "A—(SP—X)hd n" to -- A—(Sp—X)n --.

In column 7, between lines 9 and 10, insert -- Brief Description of the Sequences --.

In column 7, line 44, "Aspergillus niger" should be -- *Aspergillus niger* --.

In column 8, line 4, after "8" insert -- ) --.

In column 8, line 40, change "O" to -- 0 --.

In column 8, line 60, change "Gly" to -- Gln --.

In column 8, line 66, after "Expression" change "." to -- , --.

In column 8, line 67, change "CyS " -- Cys --.

UNITED STATES PATENT AND TRADEMARK OFFICE
CERTIFICATE OF CORRECTION

Page 2 of 3

PATENT NO. : 5,834,224
DATED : November 10, 1998
INVENTOR(S) : Petra Ruger, et al.

It is certified that error appears in the above-identified patent and that said Letters Patent is hereby corrected as shown below:

In column 9, line 28, change "Eluent" to -- Eluant --.

In column 9, line 48, after "in" insert -- "B." --.

In Claim 1, column 15, line 10, after "metal" insert -- surface, --.

In Claim 1, column 15, line 12, after "comprising" insert -- a --.

In Claim 1, column 15, line 14, after "binding", change "mol" to -- molecule --.

In Claim 1, column 15, line 20, after "ionic bond" insert -- , --.

In Claim 1, column 15, line 23, after "coverage" insert -- , --.

In Claim 5, column 15, line 36, change "molecules" to -- molecule --.

In Claim 10, column 15, line 52, before "or N- or C-terminus" insert -- C-terminus, --.

In Claim 11, column 15, line 59, after "molecule" delete -- - --.

UNITED STATES PATENT AND TRADEMARK OFFICE
CERTIFICATE OF CORRECTION

PATENT NO. : 5,834,224
DATED : November 10, 1998
INVENTOR(S) : Petera Ruger, et al.

It is certified that error appears in the above-identified patent and that said Letters Patent is hereby corrected as shown below:

In Claim 12, column 15, line 66, after the first instance of "glutamate" insert -- residue --.

In Claim 13, column 16, line 13, after the first instance of "residue" insert --,--.

In Claim 16, column 16, line 27, after "ion" delete -- - --.

In Claim 21, column 16, line 45, delete "where n" and insert therefor -- wherein --.

In Claim 25, column 16, last line, after the first instance of "material" insert --,--.

In Claim 25, column 18, line 1, between "C" and "terminus" insert -- - --.

Signed and Sealed this

Twenty-second Day of February, 2000

Attest:

Q. TODD DICKINSON

Attesting Officer

Commissioner of Patents and Trademarks